United States Patent
Buchert et al.

(10) Patent No.: US 10,638,995 B2
(45) Date of Patent: May 5, 2020

(54) IMAGING-BASED BIOMARKER FOR CHARACTERIZING THE STRUCTURE OR FUNCTION OF HUMAN OR ANIMAL BRAIN TISSUE AND RELATED USES AND METHODS

(71) Applicant: JUNG DIAGNOSTICS GMBH, Hamburg (DE)

(72) Inventors: Ralph Buchert, Berlin (DE); Jochen Fiebach, Berlin (DE); Elisabeth Steinhagen-Thiessen, Berlin (DE); Kerstin Ritter, Berlin (DE); Lothar Spies, Hamburg (DE); Joachim Seybold, Berlin (DE); Per Suppa, Berlin (DE); Catharina Lange, Berlin (DE)

(73) Assignee: JUNG DIAGNOSTICS GMBH, Hamburg (DE)

( * ) Notice: Subject to any disclaimer, the term of this patent is extended or adjusted under 35 U.S.C. 154(b) by 792 days.

(21) Appl. No.: 15/344,553

(22) Filed: Nov. 6, 2016

(65) Prior Publication Data
US 2017/0128032 A1    May 11, 2017

(30) Foreign Application Priority Data
Nov. 6, 2015    (DE) .................. 10 2015 221 877

(51) Int. Cl.
| A61B 5/05 | (2006.01) |
| A61B 6/00 | (2006.01) |
| A61B 5/00 | (2006.01) |
| G06T 7/62 | (2017.01) |
| G06T 7/11 | (2017.01) |

(Continued)

(52) U.S. Cl.
CPC .......... *A61B 6/5217* (2013.01); *A61B 5/0042* (2013.01); *A61B 5/055* (2013.01); *A61B 5/0515* (2013.01); *A61B 5/4064* (2013.01); *A61B 6/037* (2013.01); *A61B 6/508* (2013.01); *G06T 7/0012* (2013.01); *G06T 7/11* (2017.01); *G06T 7/62* (2017.01); *A61B 2576/026* (2013.01); *G06T 2207/10088* (2013.01); *G06T 2207/10104* (2013.01); *G06T 2207/30016* (2013.01);

(Continued)

(58) Field of Classification Search
None
See application file for complete search history.

(56) References Cited

U.S. PATENT DOCUMENTS

| 6,366,797 B1 | 4/2002 | Fisher et al. |
| 7,995,825 B2 | 8/2011 | Jack et al. |

(Continued)

OTHER PUBLICATIONS

Apostolova et al., "Quantitative assessment of the asphericity of pretherapeutic FDG uptake as an independent predictor of outcome in NSCLC", BMC Cancer, vol. 14, Issue 896, Dec. 2014, pp. 10.

(Continued)

*Primary Examiner* — Joel F Brutus
(74) *Attorney, Agent, or Firm* — Maschoff Brennan

(57) ABSTRACT

The invention relates to novel imaging-based biomarkers for characterizing the structure or function of a human or animal brain. These biomarkers can be a weighted confluency sum score (WCSS) or a percent shielding by brain lesions (SbBL). Methods implementing these biomarkers are also disclosed.

9 Claims, 6 Drawing Sheets

(51) Int. Cl.
*A61B 5/055* (2006.01)
*A61B 6/03* (2006.01)
*G06T 7/00* (2017.01)

(52) U.S. Cl.
CPC ............... *G06T 2207/30096* (2013.01); *G06T 2207/30204* (2013.01)

(56) References Cited

U.S. PATENT DOCUMENTS

| | | |
|---|---|---|
| 8,112,144 B2 | 2/2012 | Yamamoto et al. |
| 8,423,118 B2 | 4/2013 | Wenzel et al. |
| 2002/0012478 A1* | 1/2002 | Thirion ................ G06T 3/0068 382/294 |
| 2003/0088177 A1 | 5/2003 | Totterman et al. |

OTHER PUBLICATIONS

Apostolova et al., "Asphericity of pretherapeutic tumour FDG uptake provides independent prognostic value in head-and-neck cancer", European Radiology, vol. 24, Issue 9, Sep. 2014, pp. 2077-2087.

Glodzik et al., "Reduced glucose uptake and Aβ in brain regions with hyperintensities in connected white matter", NeuroImage, vol. 100, Oct. 15, 2014, pp. 684-691.

Hernández et al., "New multispectral MRI data fusion technique for white matter lesion segmentation: method and comparison with thresholding in FLAIR images", European Radiology, vol. 20, Issue 7, Jul. 2010, pp. 1684-1691.

Hofheinz et al., "Increased evidence for the prognostic value of primary tumor asphericity in pretherapeutic FDG PET for risk stratification in patients with head and neck cancer", European Journal of Nuclear Medicine and Molecular Imaging, vol. 42, Issue 3, Mar. 2015, pp. 429-437.

Kapeller et al., "Visual Rating of Age-Related White Matter Changes on Magnetic Resonance Imaging: Scale Comparison, Interrater Agreement, and Correlations With Quantitative Measurements", Stroke, vol. 34, Issue 2, Feb. 2003, pp. 441-445.

Kochunov et al., "Loss of cerebral white matter structural integrity tracks the grey matter metabolic decline in normal aging", NeuroImage, vol. 45, Issue 1, Mar. 1, 2009, pp. 17-28.

Prins et al., "Measuring progression of cerebral white matter lesions on MRI: Visual rating and volumetrics", Neurology, vol. 62, Issue 9, May 11, 2004, pp. 1533-1539.

Ramirez et al., "Lesion Explorer: A comprehensive segmentation and parcellation package to obtain regional volumetrics for subcortical hyperintensities and intracranial tissue", NeuroImage, vol. 54, Issue 2, Jan. 15, 2011, pp. 963-973.

Reed et al., "Effects of white matter lesions and lacunes on cortical function", Arch Neurol, vol. 61, Issue 10, Oct. 2004, pp. 1545-1550.

Schmidt et al., "An automated tool for detection of FLAIR hyperintense white-matter lesions in Multiple Sclerosis", NeuroImage, vol. 59, Issue 4, Feb. 2012, pp. 3774-3783.

Tullberg et al., "White matter lesions impair frontal lobe function regardless of their location", Neurology, vol. 63, Issue 2, Jul. 27, 2004, pp. 246-253.

Heuvel et al., "Measuring Longitudinal White Matter Changes: Original Research Comparison of a Visual Rating Scale with a Volumetric Measurement", AJNR Am J Neuroradiol, vol. 27, Issue 4, Apr. 2006, pp. 875-878.

Wahlund et al., "A New Rating Scale for Age-Related White Matter Changes Applicable to MRI and CT" Stroke, vol. 32, Issue 6, Jun. 2001, pp. 1318-1322.

Wardlaw et al., "Neuroimaging standards for research into small vessel disease and its contribution to ageing and neurodegeneration", Lancet Neurol, vol. 12, Issue 8, Aug. 2013, pp. 822-838.

* cited by examiner

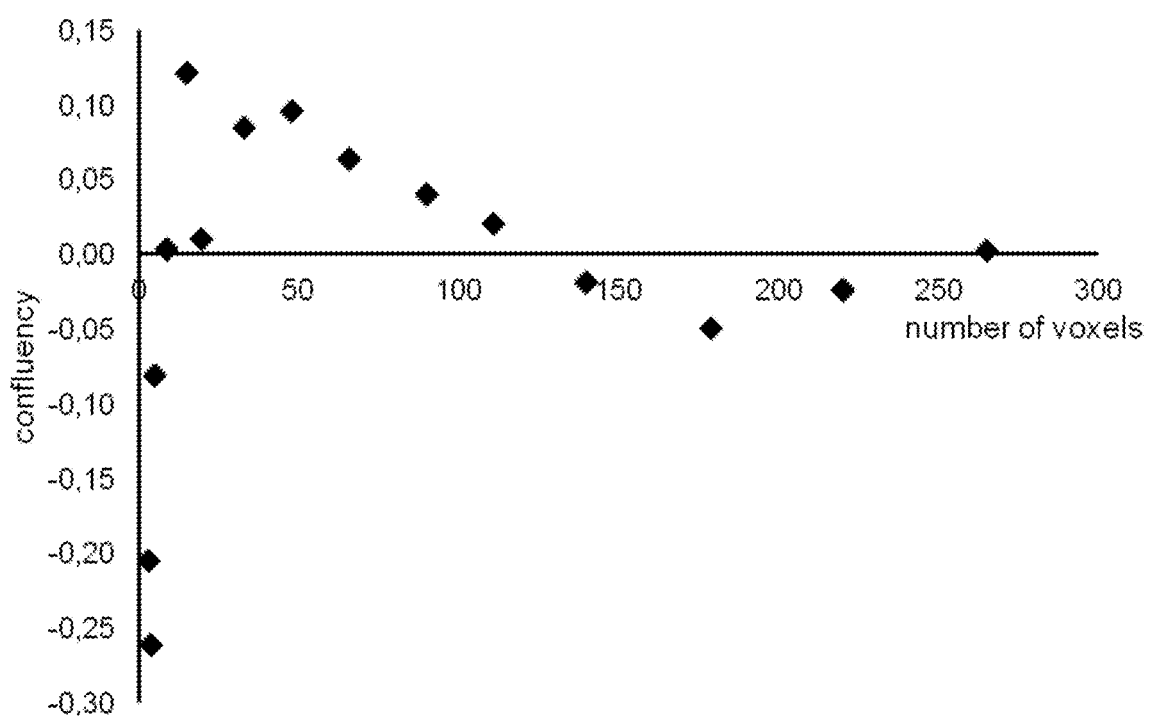
FIG 3
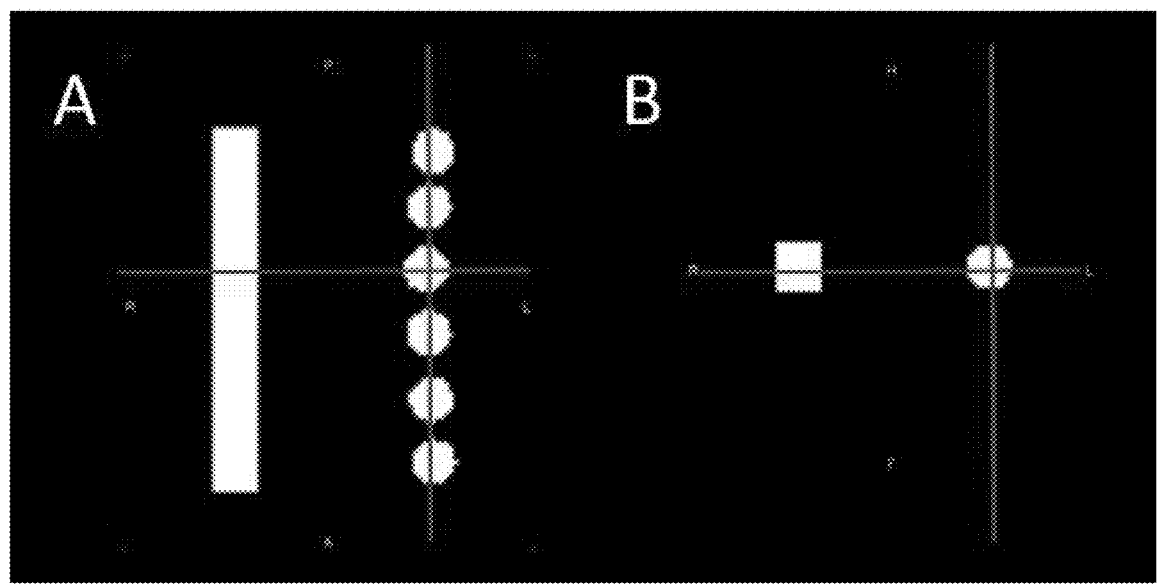
FIG 4A                    FIG 4B

Hypometabolism
Shielding of hypometabolic areas by WMH
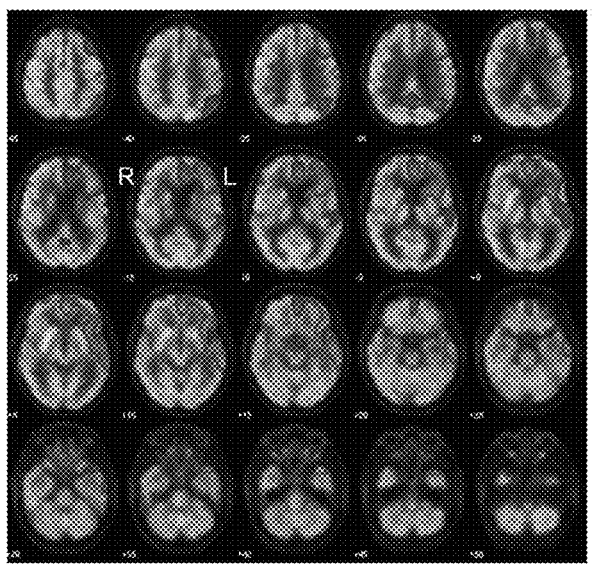
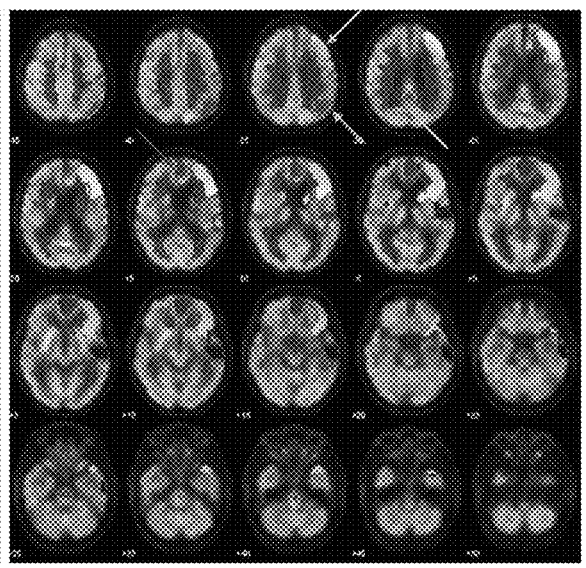
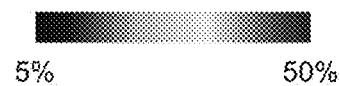
5%  50%
FIG 9A
FIG 9B
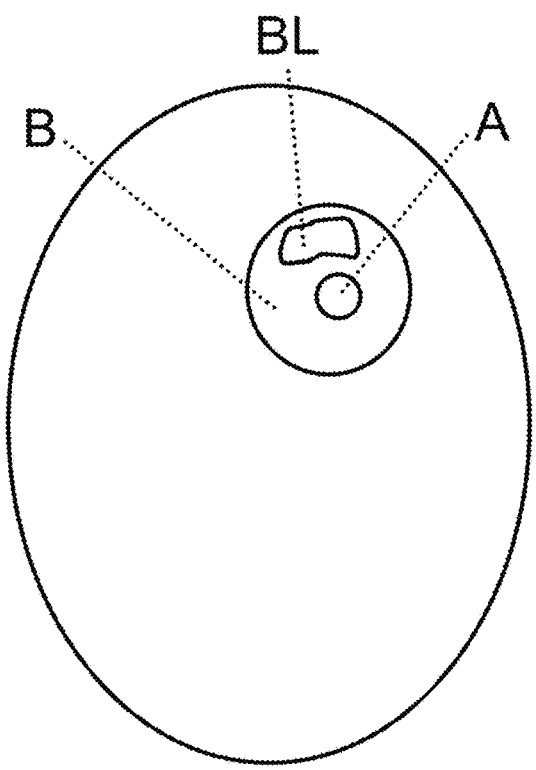
FIG 10

IMAGING-BASED BIOMARKER FOR CHARACTERIZING THE STRUCTURE OR FUNCTION OF HUMAN OR ANIMAL BRAIN TISSUE AND RELATED USES AND METHODS

CROSS-REFERENCE TO RELATED APPLICATION

This application claims priority to German Patent Application No. 10 2015 221 877.5 filed on Nov. 6, 2015, the entirety of which is incorporated by reference herein.

BACKGROUND

The instant invention relates to an imaging-based biomarker for characterizing the structure or function of human or animal brain tissue and to two methods for characterizing the structure or function of human or animal brain tissue by using such a biomarker.

Biomarkers, especially biomarkers derived from magnetic resonance (MR), positron emission tomography (PET) or magnetic particle images, allow detection and quantitative characterization of structural or functional alterations of the human or animal brain which can occur in association with various diseases including, but not restricted to cerebrovascular, neurodegenerative, and inflammatory diseases. By this, biomarkers based on these imaging modalities may support diagnosis, therapy planning and therapy monitoring in clinical routine patient care. Such biomarkers may also play an important role in the development of new treatments, new drugs and non-pharmacological treatment options, not only by supporting the inclusion of appropriate patients into clinical trials but also by providing objective outcome measures for the evaluation of therapy effects.

Biomarkers contribute to improved accuracy of a diagnosis compared to conventional clinical diagnosis using only symptom-based criteria. This is achieved by providing evidence of the patho-physiological changes in the brain characteristic for the underlying disease.

Cerebrovascular diseases' is the umbrella term for diseases that affect blood vessels supplying and draining the brain. Cerebrovascular diseases can affect small and/or large vessels. Cerebrovascular disease can be detected in MR images of the brain in which it manifests with a variety of different structural lesions including (but not restricted to) large infarcts, recent small subcortical infarcts, lacunes, subcortical hyperintensities, perivascular spaces, microbleeds, and brain atrophy [1].

MR imaging generally allows detection and quantitative characterization of structural lesions in the human or animal brain including (but not restricted to) those associated with cerebrovascular disease.

For example, subcortical hyperintensities are per definition present as hyperintensities in T2-weighted MR images and are located within the brain's white matter or in subcortical grey matter or in the brainstem. Thus, subcortical hyperintensities are lesions (within the specified brain regions) that appear brighter than normal in T2-weighted MR images. They can be easily detected by visual inspection of T2-weighted MR images (see FIG. 1A).

Structural lesions in the brain very commonly occur in older age so that virtually all elderly people show structural brain lesions, although in a strongly variable extent. Structural brain lesions can be associated with the whole spectrum of cognitive decline/dysfunction, ranging from subjective cognitive decline over mild cognitive impairment to dementia affecting activities of daily living. However, structural brain lesions can be present also without causing any symptoms. Thus, it is an important diagnostic problem to decide whether the structural brain lesions detected in a given patient are the cause of his cognitive decline or not. In the latter case, the patient should be referred to further diagnostic tests in order to identify the underlying disease, for example Alzheimer's disease.

The reliable detection of the cause of cognitive decline, for example the differentiation between vascular cognitive decline and Alzheimer's disease, has immediate therapeutic consequences: reducing risk factors in order to avoid progression in vascular cognitive decline versus cholinesterase inhibitors in Alzheimer's disease. Another, clinically highly relevant diagnostic problem is the estimation of the risk associated with detected structural brain lesions, for example the risk of cognitive decline or the risk of stroke in the future.

There is increasing evidence in the scientific literature that the pattern of the brain lesion load provides information that is relevant to both questions, i.e. differential diagnosis and risk stratification.

Nevertheless, in clinical routine patient care brain lesion load is usually assessed only qualitatively or using a visual scoring system [2]. However, these visual scores have been shown to be quite variable not only between different raters (low inter-rater stability) but also when the same rater repeats the scoring of the same image (low intra-rater stability). This clearly limits the usefulness of these visual scores.

Quantitative assessment of structural brain lesions was previously performed by manual lesion delineation, by automatic lesion segmentation algorithms or by a combination of both [3-8]. Most of the described semi-automatic software tools provide the option for localization of detected lesions, both on the basis of brain regions predefined in an anatomical standard (atlas) space or by using parcellation techniques.

It is further known from prior art to define an 'asphericity' of a tumor in whole body positron emission tomography (PET) with the glucose analog [F-18]-fluorodeoxyglucose (FDG) [9-11]. The asphericity in FDG PET is a measure of the shape irregularity of the metabolically active part of the tumor and has been proposed to predict the survival time of tumor patients. The asphericity is applied to a single tumor lesion. It has not been applied to several lesions or lesion patterns. As a consequence, the asphericity of a tumor has never been weighted in any way.

Positron emission tomography of the brain with the glucose analog F-18-fluorodeoxyglucose (FDG PET) provides biomarkers for altered (synaptic) brain function. Alterations of brain function can be caused by loss/dysfunction of neurons indicative of a neurodegenerative disease, e.g. Alzheimer's disease (AD).

U.S. Pat. No. 6,366,797 B1 describes a method of analyzing magnetic resonance images of a brain to determine the severity of a medical condition by calculating a ratio between the brain volume and volume of a specific area within the brain.

U.S. Pat. No. 7,995,825 B2 describes a method of classifying tissue in a magnetic resonance image by constructing a pixel intensity histogram of a previously acquired magnetic resonance image and applying a statistical regression analysis to the histogram to determine a pixel intensity threshold value for segmenting the histogram into at least two regions.

US 2003/0088177 A1 describes a method for assessing a neurological condition of a patient by identifying a biomarker of the nervous system of the patient in a three-dimensional image and by storing an identification of the biomarker and a quantitative measurement thereof in a storage medium. The biomarker can be a shape, topology, and morphology of brain lesions, of brain plaques, of brain ischemia, or of brain tumors; a spatial frequency distribution of sulci and gyri; a compactness of grey matter and white matter; whole brain characteristics; grey matter characteristics; white matter characteristics; cerebral spinal fluid characteristics; hippocampus characteristics; brain sub-structure characteristics; a ratio of cerebral spinal fluid volume to grey matter and white matter volume; and a number and volume of brain lesions.

U.S. Pat. No. 8,112,144 B2 describes a cerebral atrophy assessment device that is arranged and designed to calculate a numerical value representing a volume of a convex hull of the grey matter or the white matter of a brain, and to calculate a value of a first ratio between this numerical value and a numerical value representing the brain volume. Afterwards, a cerebral atrophy is assessed from the value of the first ratio.

U.S. Pat. No. 8,423,118 B2 describes a system for automated differential diagnosis of dementia, including a knowledge base that comprises a plurality of brain scan images exhibiting patterns of a plurality of types and degrees of dementia and one or more healthy brain scan images, wherein diagnosis information can be output by the system that includes an image of the patient's brain scan image with highlighted hypo-metabolic regions, wherein the highlighting is color-coded to indicate a type of dementia, wherein different colors correspond to different types of dementia.

The impact of structural brain lesions including white matter hyperintensities (WMHs) on cerebral glucose metabolism is well-documented in the literature. Kochunov et al (2009) [12] documented the association between WMH burden and global reduced cerebral glucose metabolism. Tullberg et al. (2004) [13] and Reed et al. (2004) [14] found a strong association between WMHs and a regional decline in cerebral glucose metabolism most pronounced in the frontal lobes. A recent work by Glodzik et al. (2014) [15] demonstrated that disruption of white matter tracts connecting grey matter regions caused by structural brain lesions results in a decline in glucose metabolism in connected grey matter regions.

SUMMARY

It is an object of the instant invention to provide novel imaging-based biomarkers that provide more reliable results than biomarkers known from prior art when characterizing the structure or function of human or animal brain tissue. It is a further object of the instant invention to provide methods implementing the use of the biomarkers.

This object is addressed by an imaging-based biomarker having the features as described herein. Such a biomarker is suited for characterizing the structure or function of human or animal brain tissue, in particular of a human or animal brain or parts thereof. Thereby, it is particularly suited to characterize abnormal brain tissue, i.e. brain tissue containing unusual (altered in comparison to a healthy standard population) or diseased cells or areas.

The imaging-based biomarker is based on an image of the brain tissue (e.g. of a brain or a part of a brain in its native surrounding, i.e. within a head of a living subject), the image showing at least one brain lesion and containing information on a surface and a volume of the brain lesion (in particular, if a three-dimensional image is considered) or on a circumference and an area of the brain lesion (in particular, if a two-dimensional image is considered). A plurality of brain lesions constitutes a lesion map which is a suited image within the framework of the instant disclosure.

The biomarker is chosen from the group consisting of a weighted confluency sum score (WCSS) and a percent shielding by brain lesions (SbBL). Thereby, WCSS is a weighted sum of a measure for a relationship between the surface area and the volume of brain lesions (if a three-dimensional image is considered) or between a circumference and an area of brain lesions (if a two-dimensional image is considered) over at least one identified brain lesion. Specifically, the weighted confluency sum score is a sum of weighted confluencies over at least two or more brain lesions on the image.

Thereby, the confluency of a brain lesion is a measure of a relation between a surface area of the brain lesion and a volume of the brain lesion or between a circumference of the brain lesion and an area of the brain lesion.

In addition, the percent shielding by brain lesions (SbBL) of a brain area is a measure for a fraction of a surrounding of the considered brain area belonging to a brain lesion. The brain lesions can be represented on the image as single voxels or single pixels or as clusters of contiguous voxels or pixels.

The percent shielding by brain lesions is a suited marker to evaluate remote effects of brain lesions. It turned out that the higher the shielding of a selected brain area by brain lesions the higher is the (impairing) effect of these brain lesions on remote brain areas that are not part of brain lesions. This can be explained by a loss of communication possibilities between remote (and unaffected) brain areas and the brain area that is (highly) shielded by brain lesions. The brain lesions interrupt otherwise existing communication channels between the remote brain areas and the brain area that is shielded by brain lesions.

Generally, the brain lesion can be, e.g., a cortical lesion, a subcortical lesion, a hyperintensity lesion and/or a hypointensity lesion such as, e.g., a cortical hyperintensity lesion, a subcortical hyperintensity lesion, a cortical hypointensity lesion or a subcortical hypointensity lesion.

In an embodiment, the weighted confluency sum score is proportional to the (cubic) root of the ratio between the optionally exponentiated surface of the brain lesion and the optionally exponentiated volume of the brain lesion, e.g.:

$$WCSS \sim \sqrt[z]{\frac{surface^x}{volume^y}}$$

wherein
 x is 1, 2, 3 or 4,
 y is 1, 2, 3 or 4, and
 z is 2, 3 or 4.

Suited examples of formulae for calculating the weighted confluency sum score are:

$$WCSS \sim \sqrt{\frac{surface}{volume}} \quad WCSS \sim \sqrt{\frac{surface^2}{volume^2}} \quad WCSS \sim \sqrt{\frac{surface^2}{volume}}$$

$$WCSS \sim \sqrt[3]{\frac{surface^3}{volume}} \quad WCSS \sim \sqrt[3]{\frac{surface^3}{volume^3}} \quad WCSS \sim \sqrt[3]{\frac{surface^3}{volume^2}}$$

In an embodiment, the weighted confluency sum score is proportional to the root of the ratio between the optionally exponentiated circumference of the brain lesion and the optionally exponentiated area of the brain lesion, e.g.:

$$WCSS \sim \sqrt[z]{\frac{circumference^x}{area^y}}$$

wherein
x is 1, 2, 3 or 4,
y is 1, 2, 3 or 4, and
z is 2, 3 or 4.

Suited examples of formulae for calculating the weighted confluency sum score are:

$$WCSS \sim \sqrt{\frac{circumference}{area}} \quad WCSS \sim \sqrt{\frac{circumference^2}{area^2}}$$

$$WCSS \sim \sqrt{\frac{circumference^2}{area}}$$

In an embodiment, the weighted confluency sum score is calculated according to formula (I):

$$WCSS = \sum_i w_i \cdot confluency_i \tag{I}$$

The so-called confluency$_i$ referred to in formula (I) is a measure for the sphericity of individual brain lesions. It is calculated in an embodiment according to formula (II) or to formula (III):

$$confluency_i = \sqrt[3]{\frac{1}{36 \cdot \pi} \cdot \frac{surf_i^3}{vol_i^2}} - 1 \tag{II}$$

$$confluency_i = \sqrt{\frac{1}{4 \cdot \pi} \cdot \frac{circf_i^2}{area_i}} - 1 \tag{III}$$

Thereby,
WCSS stands for weighted confluency sum score,
i is a summation index running over all or any subset of the brain lesions depicted on the image of the brain tissue,
$w_i$ is a weighting factor quantifying the relevance of the i$^{th}$ brain lesion for a considered application,
$surf_i$ represents an estimate of the surface area of the i$^{th}$ brain lesion,
$vol_i$ represents an estimate of the volume of the i$^{th}$ brain lesion,
$circf_i$ represents an estimate of the circumference of the i$^{th}$ brain lesion, and
$area_i$ represents an estimate of the area of the i$^{th}$ brain lesion.

In an embodiment, the percent shielding by brain lesions of a brain area (denoted as A) is computed as the percentage of image voxels (in particular in case of a three-dimensional image) or image pixels (in particular in case of a two-dimensional image) belonging to a brain lesion in a pre-defined volume or area (denoted as B) surrounding the considered brain area.

In an embodiment, the percent shielding by brain lesions is a percent shielding by white matter hyperintensities. In an embodiment, this is calculated according to the following formula (IV):

$$SbWMH_A = 100 * \frac{V_B(WMH)}{V_B} \tag{IV}$$

Thereby,
$SbWMH_A$ stands for percent shielding of brain region A by white matter hyperintensities (WMHs), and
$V_B$ stands for the total number of voxels or pixels in brain area B surrounding A
$V_B(WMH)$ stands for the number of voxels or pixels in brain area B belonging to a WMH In contrast to prior art, the weighted confluency sum score (WCSS) makes use of a weighting of individual observed brain lesions according to their significance. From prior art, no such weighting of individual observed brain lesions has been described. In addition, prior art does not give any suggestion to calculate a sum score of a confluency of several individual brain lesions to obtain a biomarker. In fact, no biomarker has been described in prior art that describes the pattern of a degree of confluency of brain lesions in the brain, as, e.g., observed in magnetic resonance images.

The novel biomarkers described here each allow quantitative and rater-independent characterization of the structure of the analyzed brain, in particular of brain lesions and thus of brain lesion load in the analyzed brain. They also allow the quantitative and rater-independent characterization of the impact of the brain lesion load on the function of the analyzed brain.

According to prior art, the total volume (in ml) of brain lesions throughout the whole brain is considered to be of particular relevance. However, within the scope of this invention, it was found out that the shape of brain lesions and their location within the brain appear to provide additional useful information.

The novel biomarkers provide information that is independent of the total volume of brain lesions and, therefore, might be particularly useful in combination with the total volume of brain lesions (multivariate model).

The used image can be a two-dimensional or three-dimensional image. In case of a two-dimensional image, such as an image of a (virtual) section through a brain, it is often known which depth can be assigned to this section. With this depth information, the two-dimensional image can also be regarded as three-dimensional image. In addition, a stack of several two-dimensional images can be mapped together in order to generate a (virtual) three-dimensional image of the brain or part of the brain. All these techniques are well known for a person skilled in the art.

Prior art, in particular literature references [12] to [15], do not suggest at all that the shielding of cortical grey matter by brain lesions such as WMH could be used as a biomarker. However, it will become apparent from the instant disclosure that a percent shielding by brain lesions such as white matter hyperintensities is a very well suited biomarker, e.g., to characterize the impact of cerebrovascular white matter disease on cortical glucose metabolism.

In an embodiment, the biomarker SbBL is based on the detection of brain lesions in fluid-attenuated inversion recovery magnetic resonance imaging (FLAIR-MRI) as a marker of impairment of axonal connections. The shielding expressed by the biomarker SbBL can, e.g., be used for quantitative characterization of the impact of impaired axonal connections on cortical brain activity as measured by FDG PET.

In an embodiment, the animal brain is the brain of a mammal, in particular of a rodent. Thus, the biomarkers can also be used for characterization of the structure or function of the brain in preclinical research (animal imaging).

In an embodiment, the confluency as defined according to formula (II) is scaled such that the confluency is 0 for a sphere and larger than 0 for all other shapes. In practice, the computation of the confluency is limited by the fact that images are composed of voxels with a given voxel size. Thus, there is no perfect sphere in images, but only 'edgy' approximations of a sphere composed of cubic voxels. Computer simulations that will be explained in more details below with respect to the Figures showed that the resulting error in the confluency can be neglected for spheres composed of at least 100 voxels. In an embodiment, the brain lesions therefore comprise at least 100 voxels or pixels, in particular at least 150 voxels or pixels, in particular at least 200 voxels or pixels, in particular at least 250 voxels or pixels, in particular at least 300 voxels or pixels, in particular at least 350 voxels or pixels, in particular at least 400 voxels or pixels, in particular at least 450 voxels or pixels and very particular at least 500 voxels or pixels on the image.

Since brain lesions are regularly defined by their occurrence and detectability in images obtained by magnetic resonance imaging, the analyzed image is, in an embodiment, a magnetic resonance image. A suited recordation variant for recording such a magnetic resonance image is fluid-attenuated inversion recovery (FLAIR) magnetic resonance imaging.

Alternatively, the image can be obtained by magnetic particle imaging or by positron emission tomography.

While different kinds of magnetic resonance images could be generally used to detect brain lesions, T1-weighted and/or T2 (including FLAIR)-weighted and/or T2*-weighted magnetic resonance images are particularly suited for detecting brain lesions.

In an aspect, the invention relates to the use of the imaging-based biomarker according to the preceding explanations for characterizing the structure or function of a human or animal brain on the basis of an analysis of the image of the brain. Thereby, the image is suited to detect brain lesions on it. These brain lesions may be, e.g., white matter hyperintensities or grey matter hypo- or hyperintensities.

In an aspect, the invention also relates to a method for characterizing the structure or function of human or animal brain tissue on the basis of an analysis of the image of the brain tissue by using the imaging-based biomarker according to the preceding explanations. Thereby, the image is suited to detect brain lesions on it.

In an aspect, the invention relates to the use of the imaging-based biomarker according to the preceding explanations for characterizing a brain lesion load in human or animal brain tissue on the basis of an analysis of an image of the brain tissue. Thereby, the image is suited to detect brain lesions on it.

In an aspect, the invention also relates to a method for characterizing a brain lesion load in human or animal brain tissue on the basis of an analysis of the image of the brain tissue by using the imaging-based biomarker according to the preceding explanations. Thereby, the image is suited to detect brain lesions on it.

In an aspect, the invention relates to the use of the imaging-based biomarker according to the preceding explanations for diagnosing a disease, for differentiating between different diseases (differential diagnosis), in particular for differentiating between a neurodegenerative disease and a cerebrovascular disorder of a subject, or for monitoring the time course of a change of brain structure or function, with or without treatment on the basis of an analysis of an image of brain tissue, such as of the brain. Thereby, the image is suited to detect brain lesions on it.

In an aspect, the invention also relates to a method for diagnosing a disease, for differentiating between different diseases (differential diagnosis), in particular for differentiating between a neurodegenerative disease and a cerebrovascular disorder of a subject, or for monitoring the time course of a change of brain structure or function, with or without treatment on the basis of an analysis of an image of brain tissue, such as of the brain, by using the imaging-based biomarker according to the preceding explanations. Thereby, the image is suited to detect brain lesions on it.

Further uses of the biomarker or methods using the biomarker relate to the detection of the cause of cognitive decline of a subject suffering from cognitive decline. Further uses of the biomarker or methods using the biomarker relate to the differentiation between a disease state that is caused by loss/dysfunction of neurons and a disease state that is caused by alterations of blood flow in the brain tissue of a subject.

In an embodiment, the neurodegenerative disease is Alzheimer's disease.

In an aspect, the invention relates to the use of the imaging-based biomarker according to the preceding explanations for an assessment or stratification of the risk associated with detected subcortical hyperintensities regarding the development of future brain disorders or brain-related diseases, such as the risk of cognitive decline or the risk of stroke within a defined period of time. This defined period of time may be, e.g., 1, 2, 3, 4, 5, 6, 7, 8, 9 or 10 years. This risk assessment or risk stratification is carried out once again on the basis of an analysis of an image of brain tissue. Thereby, the image is suited to detect brain lesions on it.

In an aspect, the invention also relates to an according method for an assessment or stratification of the risk associated with detected subcortical hyperintensities regarding the development of future brain disorders or brain-related diseases, on the basis of an analysis of the image of brain tissue by using the imaging-based biomarker according to the preceding explanations. Thereby, the image is suited to detect brain lesions on it.

In an aspect, the invention relates to a first method for characterizing the structure or function of human or animal brain tissue. Thereby, the method comprises the steps explained in the following.

In a first method step, an image of human or animal brain tissue is provided. Thereby, the image is suited to detect brain lesions on it.

In another method step, one or more brain lesions are—in particular automatically—detected on the image and their outer contour is—in particular automatically—delineated.

In another method step, a confluency is computed for each delineated brain lesion, wherein the confluency is a measure of a relation between a surface area of the brain lesion and a volume of the brain lesion or between a circumference of the brain lesion and an area of the brain lesion.

In another method step, a weighted confluency sum score is computed as a sum of weighted confluencies over each delineated brain lesion.

In another method step, the weighted confluency sum score is used to characterize the structure or function of the human or animal brain tissue, the image of which has been analyzed.

In an embodiment, a weighting factor $w_i$ is automatically assigned to each delineated brain lesion. The weighting factor $w_i$ quantifies the relevance of the $i^{th}$ lesion for the diagnostic indication of interest. The larger the weighting factor the larger the relevance of the respective lesion. The weighting factor can, e.g., take either continuous (real number) or discrete (integer or rational number) values.

The weighted confluency sum score (WCSS) does not only provide information on the confluency of the detected brain lesions, but also significance-weighted information on the relevance of the respective brain lesions. Therewith, much more significant, reliable and relevant information is obtained about the brain lesions observed in an image of the brain than according to methods known from prior art.

The method steps can be, but need not be performed in the sequence indicated above. Herewith disclosed is also any other suited method step sequence that can be applied in order to obtain the weighted confluency sum score (WCSS).

In an embodiment, the weighted confluency sum score (WCSS) is computed according to formula (I):

$$WCSS = \sum_i w_i \cdot confluency_i, \quad (I)$$

Thereby,
WCSS stands for weighted confluency sum score, and
i is a summation index running over all or any subset of brain lesions delineated on the image of the brain, In an embodiment, the confluency is calculated according to formula (II) or to formula (III):

$$confluency_i = \sqrt[3]{\frac{1}{36 \cdot \pi} \cdot \frac{surf_i^3}{vol_i^2}} - 1 \quad (II)$$

$$confluency_i = \sqrt{\frac{1}{4 \cdot \pi} \cdot \frac{circf_i^2}{area_i}} - 1 \quad (III)$$

wherein
$w_i$ is a weighting factor quantifying the relevance of the $i^{th}$ brain lesion for a considered application,
$surf_i$ represents an estimate of the surface area of the $i^{th}$ brain lesion,
$vol_i$ represents an estimate of the volume of the $i^{th}$ brain lesion,
$circf_i$ represents an estimate of the circumference of the $i^{th}$ brain lesion, and
$area_i$ represents an estimate of the area of the $i^{th}$ brain lesion.

In an embodiment, the weighting factor is different for brain lesions located within different brain regions. In doing so, the relevance of the location of the brain lesion for the specific problem to be solved is adequately regarded.

In an embodiment, the weighting factor is different for brain lesions that are located within cortical grey matter, within periventricular white matter, within deep white/grey matter, within subcortical white matter, or within the brain stem. Thereby, brain lesions that are located within the brainstem are to be considered as the most relevant brain lesions. The highest weighting factor should be assigned to these brain lesions. The second most relevant brain lesions are those located within subcortical white matter. The second highest weighting factor should be assigned to these brain lesions. The third most relevant brain lesions are located within deep white/grey matter. The third highest weighting factor should be assigned to these brain lesions. The fourth most relevant brain lesions are located within periventricular white matter. The fourth highest weighting factor should be assigned to these brain lesions.

The weighting factors assigned to the individual brain lesions can be arbitrarily chosen. In an embodiment, the weighting factor is set to be 1 if the brain lesion is located within periventricular white matter. Additionally, it is set to be 2 if the brain lesion is located within deep white/grey matter. Furthermore, it is set to be 3 if the brain lesion is located within subcortical white matter. Finally, it is set to be 4 if the brain lesion is located within the brain stem. The numerical differences between these weighting factors are sufficient to adequately weight the individual brain lesions so as to produce a significant biomarker, namely the weighted confluency sum score (WCSS).

It might be the case that a detected brain lesion is located in (or spread over) more than one brain region. In such a case, the highest weighting factor of the respective brain regions is assigned to this brain lesion in an embodiment.

In an aspect, the invention relates to a second method for characterizing the structure or function of human or animal brain tissue. Thereby, the method comprises the steps explained in the following.

In a first method step, an image of human or animal brain tissue is provided, which is suited to detect brain lesions on it.

In another method step, at least one brain lesion on the image is—in particular automatically—detected and its outer contour is—in particular automatically—delineated. Thereby, a brain lesion map is obtained.

In another method step, a percent shielding by brain lesions for at least one selected brain area is computed, wherein the percent shielding by brain lesions of the selected brain area is a measure for a fraction of the surrounding of the selected brain area belonging to a brain lesion.

In another method step, the percent shielding by brain lesions of the at least one selected brain area is used to characterize the structure or function of the human or animal brain tissue, the image of which has been analyzed.

The selected brain area can be one voxel or one pixel or it can comprise an area or a volume of, e.g., 10 ml or more, 20 ml or more, 30 ml or more, 40 ml or more, 50 ml or more, 60 ml or more, 70 ml or more, 80 ml or more, 90 ml or more, or 100 ml or more. The surrounding volume referred to above can have the same values.

In an embodiment, the selected brain areas for computing their percent shielding by brain lesions are selected according to the following method steps.

In a first method step, a second image of the same human or animal brain tissue is provided, wherein the second image is suited to provide different information about brain structure or function than the first image. To give an example, the second image might be suited to provide information on (synaptic) function and dysfunction of the brain tissue. Usually, the second image is obtained by a different imaging technique than the first image.

In another method step, the lesion map is anatomically mapped (co-registered) with the second image.

In another method step, the mapped (co-registered) lesion map and the second image are stereotactically normalized into an anatomical standard space. This anatomical standard space can also be denoted as template or atlas space. A normalized second image is obtained.

In another method step, the normalized second image is compared with at least one equivalent reference image from at least one reference subject to generate an effect map indicating brain areas in which a property (such as an intensity) of the second image differs from the reference image. The effect map can be, e.g., a hypometabolism map indicating hypometabolic areas or voxels in the brain. This comparison can be done, in an embodiment, on the level of voxels or pixels.

In an embodiment, the comparison is a statistic comparison, leading, e.g., to a statistical parametric map of hypometabolism for the respective brain. Other comparison techniques are also possible. Instead of the single healthy control subject, a group of healthy control subjects (healthy control database) can be used for comparison.

In another method step, the percent shielding by brain lesions is computed for each brain area on the effect map.

To give an example, a percentage shielding by white matter hyperintensities can be computed for each hypometabolic voxel as fraction of neighboring (in a predefined volume) white matter voxels affected by white matter hyperintensities.

The structural or functional characterization of the brain tissue can then be used to differentiate between a cerebral vascular disease and a neurodegenerative disease. In particular, by applying the biomarker SbWMH (being an example of the biomarker SbBL) the risk of misinterpreting WMH-associated alteration in FDG PET as indication of a neurodegenerative disease is significantly reduced.

The method steps can be, but need not be performed in the sequence indicated above. Herewith disclosed is also any other suited method step sequence that can be applied in order to obtain the biomarker SbBL.

In an embodiment, the first image is recorded by structural MRI, such as FLAIR MRI or T1-weighted MRI.

In an embodiment, the second image is recorded by positron emission tomography with F-18-fluorodeoxyglucose (FDG PET).

In an embodiment, the percent shielding by brain lesions (SbBL) is computed for each pixel or voxel in the effect map and then overlaid to the second image so as to better visualize percent shielding. The resulting image can be compared to an analogous image in which the effect map is overlaid to the second image. Visual side-by-side inspection of these 2 images simplifies the interpretation of SbBL.

The methods explained above are usually carried out for assessing previously obtained images. Thus, they can also be referred to as in vitro methods. In an aspect of the instant invention, the methods explained above can alternatively or additionally be carried out during recordation of the images to be analyzed. In this aspect, the methods can also be referred to as in vivo or in situ methods.

The methods explained above are usually carried out to provide original data that can later on be used for helping a physician in making a diagnosis on a certain disorder or disease. In an aspect, the claimed methods encompass the step of making such a diagnosis.

The methods explained above can be carried out by a (computer) system for fully automatic determination of the described biomarkers, utilizing images, such as MR images, of the human or animal brain. Such a system comprises different means for carrying out the individual tasks to accomplish the method.

In an aspect, the invention relates to a computer program product that is able to carry out at least one method according to any of the preceding explanations when it is executed on a computer.

In another aspect, the invention relates to a non-transitory computer readable medium on which a brain structure assessment program is stored that causes an information processing device (such as a computer) to execute at least one method according to any of the preceding explanations.

The embodiments described above can be combined in any desired way. In addition, embodiments explained with respect to any of the described biomarkers, the described uses, the described methods and the described computer program can be transferred to any other of the described biomarkers, the described uses, the described methods and the described computer program in any desired way.

BRIEF DESCRIPTION OF THE DRAWINGS

Aspects of the invention will be explained more detail with respect to Figures and exemplary embodiments.

FIG. 3 shows the results of a computer simulation of spheres composed of a varying number of cubic voxels.

FIG. 4A shows the results of a computer simulation of a confluency sum score of differently shaped lesions in transversal view.

FIG. 4B shows the results of a computer simulation of a confluency sum score of differently shaped lesions in coronal view.

FIG. 9A shows a parametric hypometabolism map overlaid to FDG PET images of the brain of a patient.

FIG. 9B shows a parametric SbWMH map and a WMH lesion map overlaid to FDG PET images of the brain of the same patient as in FIG. 9A.

FIG. 10 shows schematically a brain area (denoted as A) shielded by a brain lesion (denoted as BL) in an area (denoted as B) surrounding the considered brain area (A).

DETAILED DESCRIPTION

Figures 1A, 1B:
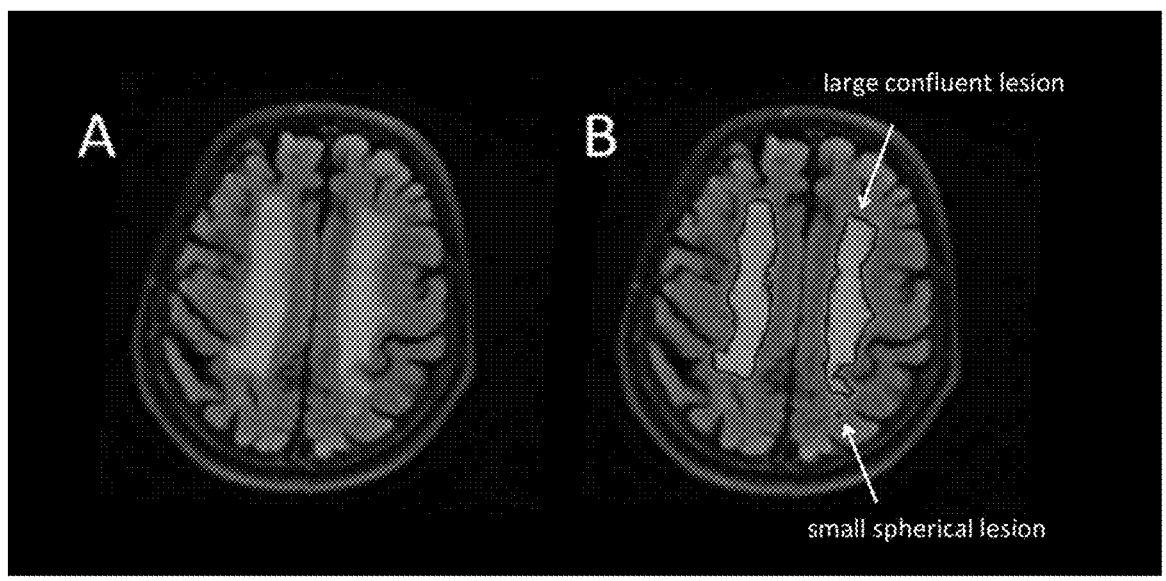
FIG. 1A shows a transversal slice of a FLAIR-MR image without delineation of subcortical hyperintensities.
FIG. 1B shows a transversal slice of a FLAIR-MR image with delineation of subcortical hyperintensities.

FIG. 1A shows a transversal slice of a FLAIR-MR image without delineation of subcortical hyperintensities. Such transversal slices are known from prior art. FIG. 1B shows a transversal slice of a FLAIR-MR image with delineation of subcortical hyperintensities. In this Figure, a large confluent lesion can be well distinguished from a small spherical lesion.

A delineation as shown in FIG. 1B is used in a method according to the first exemplary embodiment explained in the following. FIGS. 2A to 6 will be explained with respect to this first exemplary embodiment. FIGS. 7A to 10 will be explained with respect to a second exemplary embodiment.

First Exemplary Embodiment: Calculation of a Weighted Confluency Sum Score (WCSS)

The exemplary embodiment relates to a (computer) system for fully automatic determination of a weighted confluency sum score (WCSS). This system utilizes magnetic resonance (MR) image data of the human brain. It starts with the automatic detection of all brain lesions in the MR image and accurate delineation of their outer contours. An exemplary result is shown in FIG. 1B. The system implements an algorithm for automatic detection of FLAIR-hyperintense white-matter lesions which has been proposed by Schmidt and co-workers for application in with multiple sclerosis [3].

This Schmidt algorithm generates a three-dimensional hyperintensity map which is then binarized. The binarized hyperintensity map is then clustered into separate hyperintensity lesions using the routine spm_bwlabel from the Statistical Parametric Software package (version SPM8, http://www.fil.ion.ucl.ac.uk/spm/). This routine labels connected components on the basis of a connectivity criterion to be specified. Six adjacent voxels (on the surface) have been defined here as connectivity criterion.

Then the system computes the confluency for each brain lesion according to formula (II)

$$confluency_i = \sqrt[3]{\frac{1}{36 \cdot \pi} \cdot \frac{surf_i^3}{vol_i^2}} - 1, \quad (II)$$

Surface and volume of the hyperintensity lesion are computed by counting of voxels as defined in the clustered hyperintensity map. This is computationally very efficient.

Figures 2A, 2B:
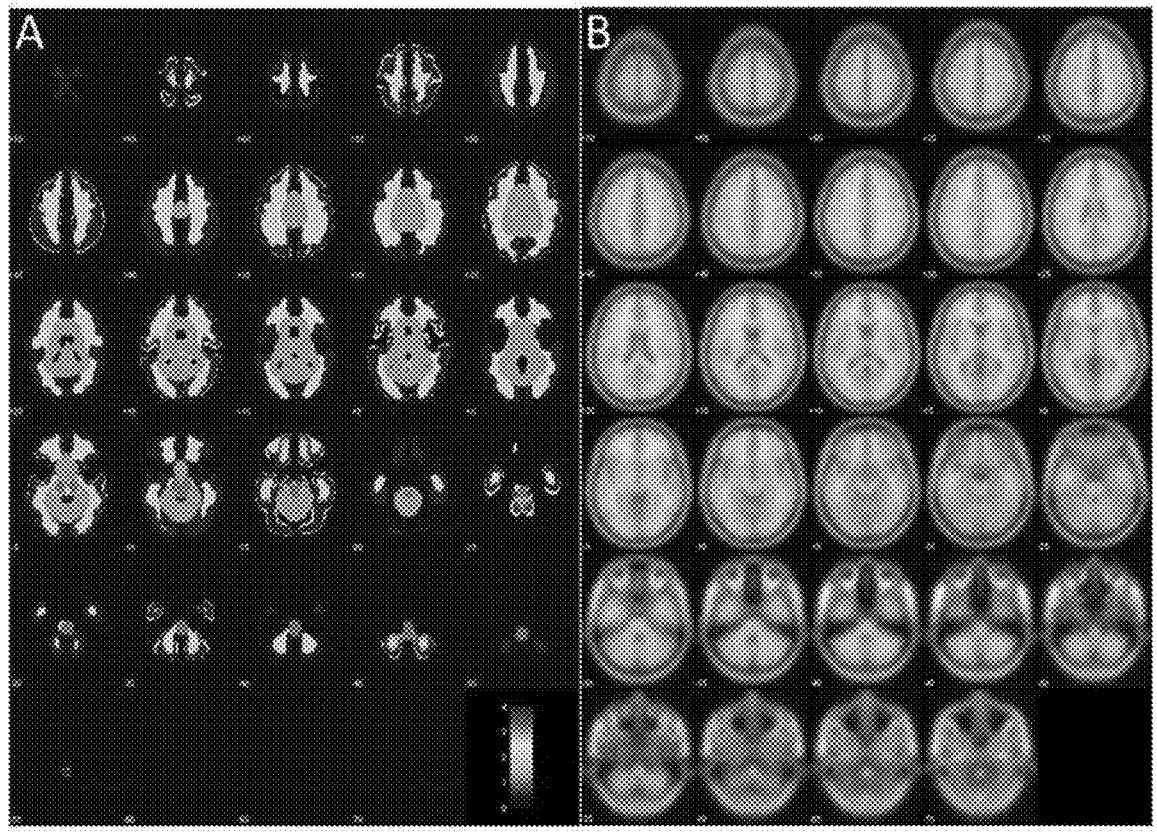
FIG. 2A shows transversal slices of an anatomical map of a brain.
FIG. 2B shows slices from a T1-weighted MR image corresponding to the slices of FIG. 2A for anatomical orientation.

The weighting factor $w_i$ for a given hyperintensity lesion is defined according to its localization within the brain: $w_i=1, 2, 3, 4$ if the lesion is located within periventricular white matter, deep white/grey matter, subcortical white matter, or within the brain stem, respectively. The assignment of the lesion to these four different regions is based on an anatomical map that has been previously created from tissue probability maps provided by SPM8. This anatomical map is depicted in FIG. 2A, wherein subcortical white matter is depicted in dark red, deep white/grey matter is depicted in green, periventricular white matter is depicted in orange and brainstem is depicted in blue. For a better anatomical orientation, FIG. 2B shows corresponding slices from a T1-weighted MR image. If a hyperintensity lesion is located in more than one of the regions, it is assigned the highest weighting factor of these lesions.

Finally, the weighted confluency sum score (WCSS) is computed according to formula (V)

$$WCSS = \sum_i^m w_i \cdot confluency_i \quad (V)$$

The individual parameters have the same meaning as in case of formula (I). The only difference between formula (I) and (V) is that in case of formula (V) m is used as number of the analyzed brain lesions. Thereby, m refers to the total number of hyperintensity lesions in the hyperintensity map consisting of at least 100 voxels.

The instantly described system has been successfully validated by the following experiments:

The algorithm proposed by Schmidt and co-workers for FLAIR-hyperintensity lesions in multiple sclerosis was successfully validated in 44 elderly patients (mean age 80 years) with unclear cognitive impairment from several wards for geriatric inpatients.

As already explained above, there is no perfect sphere in MR images, but only 'edgy' approximations of a sphere composed of cubic voxels. Computer simulations of spheres composed of a varying number of cubic voxels showed that the resulting error in the confluency can be neglected for spheres composed of at least 100 voxels. The according results are shown in FIG. 3. For spheres composed of at least 100 voxels, the confluency approaches zero, i.e. the value of an ideal sphere.

Computer simulations were performed to show that the confluency according to formula (II) indeed is a useful measure of confluency of brain lesions. Specifically, 6 spherical lesions of 10 mm radius each and one cuboid simulating the confluency of the 6 spheres to one single contiguous lesion were analyzed. The results are depicted in FIGS. 4A and 4B. The calculated WCSS was almost zero for the pattern consisting of the 6 spherical lesions, whereas it was only 0.74 for the cuboid (all weighting factors were set to 1).

Figure 5:
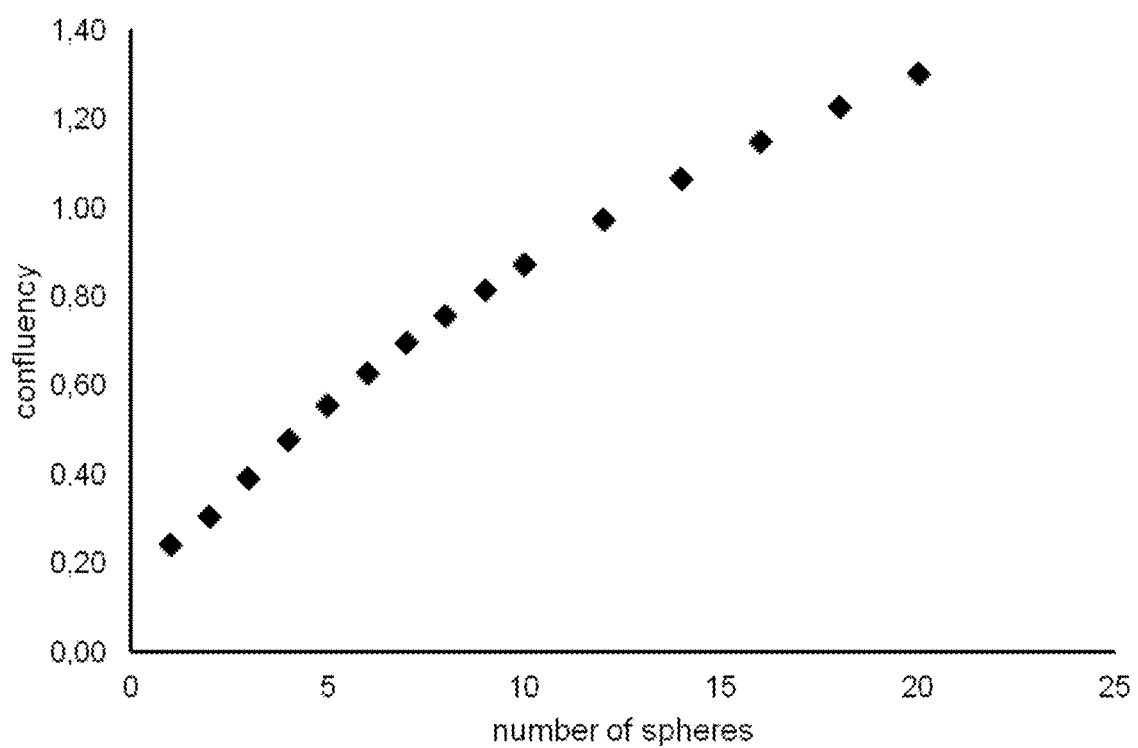
FIG. 5 shows the confluency score of cuboids having different lengths.

When the number of spherical lesions that confluenced to a cuboid was increased, the WCSS of the cuboid showed a continuous increase. The according results can be seen in FIG. 5 showing that the confluency score of a cuboid increases continuously with its length, i.e. the number of spherical lesions that confluenced to the cuboid. The WCSS of the pattern of spherical lesions remained almost zero, independent on the number of spherical lesions (all weighting factors were set to 1).

Figure 6:
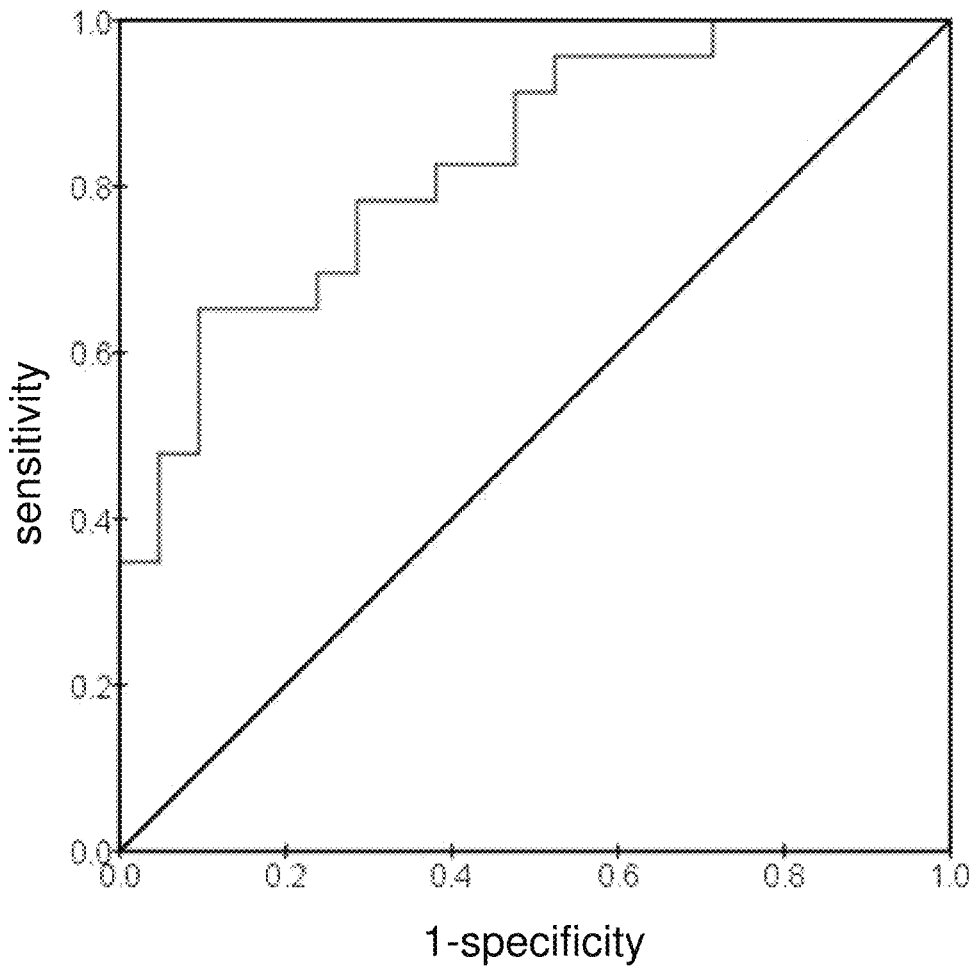
FIG. 6 shows a receiver-operating characteristic (ROC) curve of the WCSS for differentiation between patients with vascular cognitive decline and patients without relevant cerebrovascular disease.

In a clinical evaluation, the area under a receiver-operating characteristic curve for differentiation between patients with vascular cognitive decline and patients without relevant cerebrovascular disease by the WCSS was 0.830. This is shown in FIG. 6. This clearly shows that the WCSS is clinically useful.

Second Exemplary Embodiment: Calculation of a Percent Shielding by White Matter Hyperintensities (SbWMH)

Patho-physiological changes in the brain caused by neurodegenerative diseases such as Alzheimer's disease include alterations of brain activity (synaptic dysfunction). Positron emission tomography of the brain with the glucose analog F-18-fluorodeoxyglucose (FDG PET) provides biomarkers for (synaptic) function and dysfunction, as depicted in FIGS. 7A and 7B.

Figures 7A, 7B:
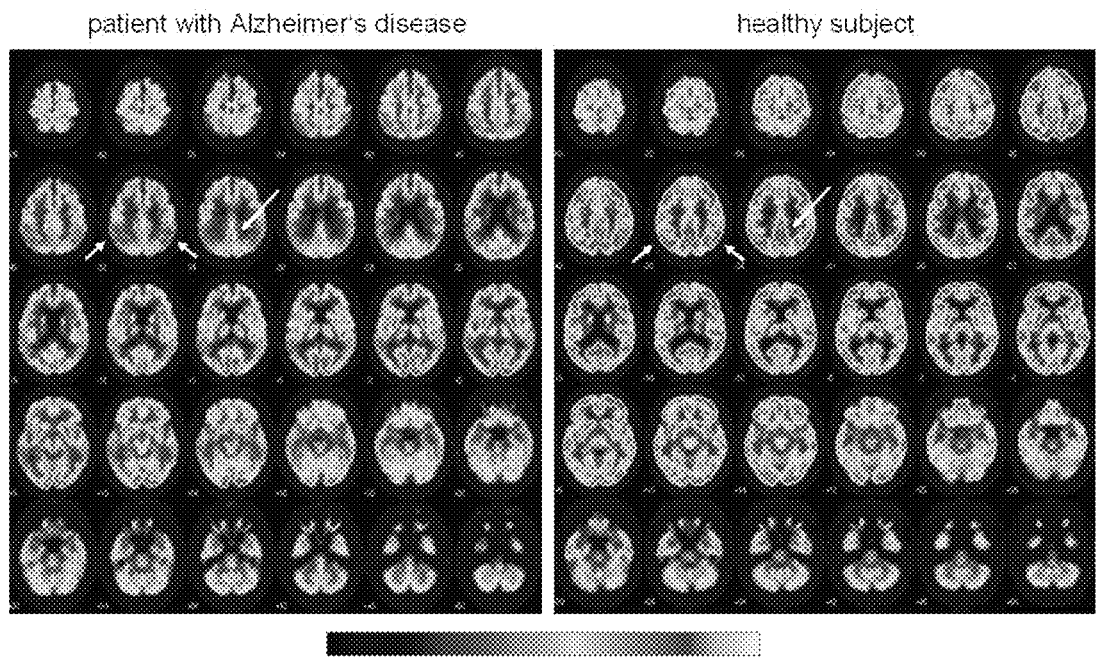
FIG. 7A shows FDG PET images of the brain in a patient with Alzheimer's disease.
FIG. 7B shows FDG PET images of the brain in a healthy subject.

FIG. 7A shows FDG PET images of the brain in a patient with Alzheimer's disease. These images show a reduction of brain activity compared to a healthy subject (cf. FIG. 7B) in most brain regions except visual and motor cortex, subcortical brain structures and the cerebellum. The reduction is most pronounced in posterior cingulum/precuneus area and the parietotemporal cortex (indicated by arrows). This pattern is typical for Alzheimer's disease. The reduction of brain activity is mainly caused by reduced synaptic activity. Although there is some loss of brain tissue (atrophy) in Alzheimer's disease, its impact on brain FDG PET is rather small, at least at early stages of the disease. In case of strong atrophy, the effect on FDG PET can be taken into account by partial volume correction.

Figures 8A, 8B:
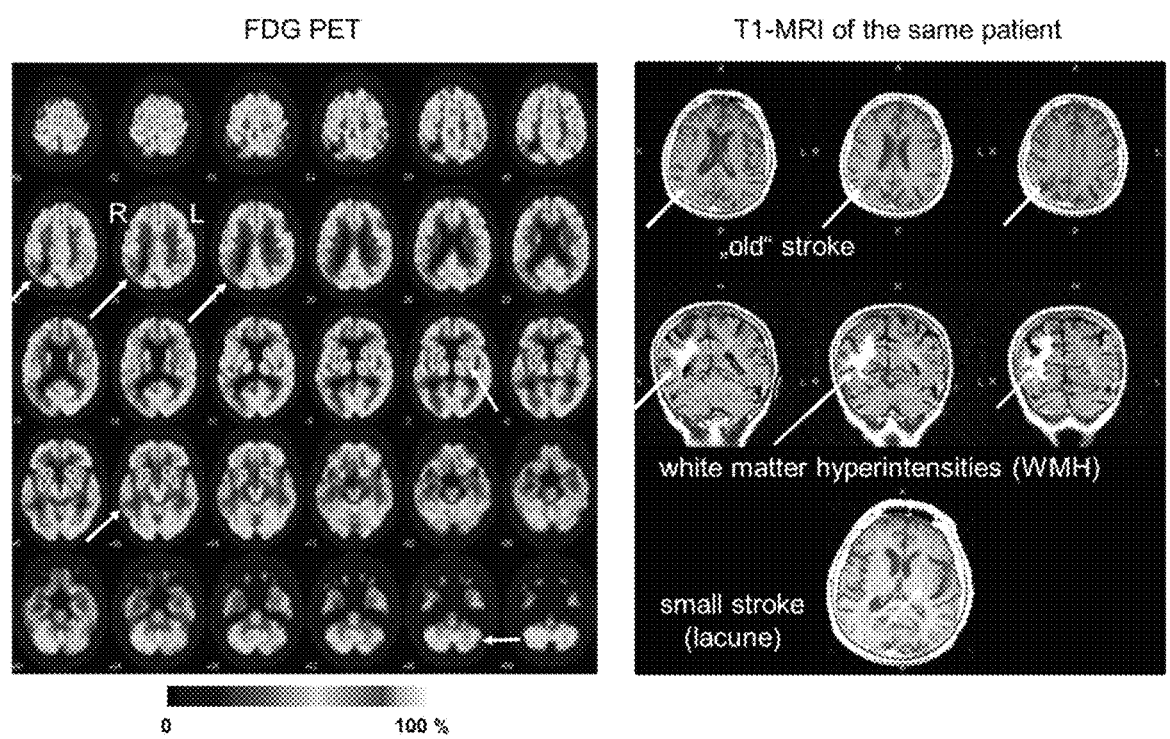
FIG. 8A shows FDG PET images of the brain in a patient who was suspected to have Alzheimer's disease.
FIG. 8B shows T1-MR images of the same patient as in FIG. 8A.

In old patients, however, the detection of synaptic dysfunction associated with neurodegenerative disease is complicated by the high rate of vascular co-morbidity, for example infarcts of the brain of varying size. This is depicted in FIGS. 8A and 8B. FIG. 8A shows brain FDG PET images in a patient who was suspected to have Alzheimer's disease. The pattern of reduction in the PET indeed looks rather similar to the typical pattern in Alzheimer's disease (cf. FIG. 7A). However, inspection of the MRI of the same patient (depicted in FIG. 8B) reveals several infarcts and strong white matter disease (indicated by arrows). This vascular pathology fully explains the abnormal findings in the FDG PET. Therefore, there is no indication of Alzheimer's disease in this patient. The patient has vascular cognitive decline.

It is evident that there is no FDG uptake in infarcted tissue (scar). Whether or not a reduction of FDG uptake is the direct consequence of an infarct can be tested rather easily by coregistering T1- and/or T2-weigthed MRI (in which most infarcts are clearly displayed) to the FDG PET. However, not only infarcts but also impairment of axonal connections can cause reduced synaptic activity in both neighboring and distant grey matter regions, due to interruption of axonal tracts to this region.

Since white matter hyperintensities are to be considered as specific brain lesions, the novel biomarker SbWMH is an embodiment of the biomarker SbBL (shielding by brain lesions). It is a marker of impairment of axonal connections in form of a percent shielding of cortical brain regions by white matter hyperintensities.

A processing pipeline for fully automated computation and display of SbWMH has been implemented as a MATLAB script. For some processing steps, tools from the statistical parametric mapping software package are used (version SPM8). The pipeline comprises the following steps.

Extraction of White Matter Hyperintensities from Structural MRI

The "Lesion Segmentation Toolbox", a freely-available add-on to SPM8, is used to extract WMHs from the patient's structural MRI. The toolbox requires a high-resolution T1-weighted MRI and a FLAIR-MRI as input. The output is a binary lesion map delineating WMHs in the patient's native space.

Co-Registration and Spatial Normalization of Lesion Map and FDG PET

SPM's co-register tool is used to register the lesion map with the FDG PET. SPM's normalize tool is used to transform co-registered images into the anatomical space of the Montreal Neurological Institute (MNI).

Generation of Hypometabolism Map

A (homoscedastic) t-test for two independent samples is used to compare the patient's normalized FDG PET to the normalized FDG PETs of a database of aged-matched healthy controls. The global FDG-uptake is used as reference value for intensity scaling prior to the statistical test. Reduced scaled FDG-uptake is defined as "hypometabolism" if $p \leq 0.001$. This results in a parametric map of hypometabolism. Such a hypometabolism map is shown in FIG. 9A depicting a parametric hypometabolism map (blue blobs) overlaid to the patient's FDG-PET.

Voxel-Wise Computation of SbWMH

The SbWMH is computed for each hypometabolic voxel as the fraction of neighboring white matter voxels affected by WMH (FIG. 10). The 50 ml white matter voxels closest to the hypometabolic voxel are used as white matter "neighborhood". White matter is defined by a binary mask that has been generated from the a priori tissue probability maps used for WMH lesion segmentation. The SbWMH values are saved to a 3-dimensional parametric map.

Display

The slover tool as implemented in SPM8 is used to display the SbWMH map (as "blobs" with "jet" colortable) together with the WMH lesion mask (as contours) superimposed to the patient's FDG PET in MNI space. An according map is shown in FIG. 9B depicting a parametric SbWMH map (jet-colored blobs) and WMH lesion map (red contours) overlaid to the FDG PET. The SbWMH values are quantitative: SbWMH=50 means that as much as 50% of the closest 50 ml white matter voxels are affected by WMH. As a consequence, the hypometabolism in this voxel most likely is caused by neighboring WMH, i.e. the hypometabolism is due to cerebrovascular disease, whereas no indication of neurodegenerative disease could be found.

In the example depicted in FIGS. 9A and 9B, the hypometabolism in the left lateral frontal cortex, the left parietotemporal cortex and in the precuneus can be explained by WMH (green arrows). The hypometabolism in the medial frontal cortex most likely is not caused by WMH, it rather might be an unspecific effect of old age (red arrow). The patient most likely does not suffer from Alzheimer's disease (AD), although the pattern of hypometabolism is similar to the typical AD pattern. Thus, in this case, the SbWMH map reduces the risk of misinterpretation the structural alterations of the brain as AD.

The basic idea underlying the percent shielding by brain lesions is illustrated in FIG. 10. The percent shielding by brain lesions of a brain area A is computed as the percentage of image voxels or image pixels belonging to a brain lesion BL in a predefined volume or area B surrounding the considered brain area A. There can be more than one brain lesion BL in the volume or area B all of which contribute to the percent shielding of A.

LIST OF REFERENCES CITED IN THE PRECEDING SECTIONS

1. Wardlaw, J. M., et al., *Neuroimaging standards for research into small vessel disease and its contribution to ageing and neurodegeneration*. Lancet Neurol, 2013. 12(8): p. 822-38.
2. Wahlund, L. O., et al., *A new rating scale forage-related white matter changes applicable to MRI and CT*. Stroke, 2001. 32(6): p. 1318-22.
3. Schmidt, P., et al., *An automated tool for detection of FLAIR-hyperintense white-matter lesions in Multiple Sclerosis*. Neuroimage, 2012. 59(4): p. 3774-83.
4. Kapeller, P., et al., *Visual rating of age-related white matter changes on magnetic resonance imaging: scale comparison, interrater agreement, and correlations with quantitative measurements*. Stroke, 2003. 34(2): p. 441-5.
5. Prins, N. D., et al., *Measuring progression of cerebral white matter lesions on MRI: visual rating and volumetrics*. Neurology, 2004. 62(9): p. 1533-9.
6. van den Heuvel, D. M., et al., *Measuring longitudinal white matter changes: comparison of a visual rating scale with a volumetric measurement*. AJNR Am J Neuroradiol, 2006. 27(4): p. 875-8.

7. Hernandez Mdel, C., et al., *New multispectral MRI data fusion technique for white matter lesion segmentation: method and comparison with thresholding in FLAIR images*. Eur Radiol, 2010. 20(7): p. 1684-91.
8. Ramirez, J., et al., *Lesion Explorer: a comprehensive segmentation and parcellation package to obtain regional volumetrics for subcortical hyperintensities and intracranial tissue*. Neuroimage, 2011. 54(2): p. 963-73.
9. Apostolova, I., et al., *Quantitative assessment of the asphericity of pretherapeutic FDG uptake as an independent predictor of outcome in NSCLC*. BMC Cancer, 2014. 14: p. 896.
10. Apostolova, I., et al., *Asphericity of pretherapeutic tumour FDG uptake provides independent prognostic value in head-and-neck cancer*. Eur Radiol, 2014. 24(9): p. 2077-87.
11. Hofheinz, F., et al., *Increased evidence for the prognostic value of primary tumor asphericity in pretherapeutic FDG PET for risk stratification in patients with head and neck cancer*. Eur J Nucl Med Mol Imaging, 2014.
12. Kochunov, P., Ramage, A. E., Lancaster, J. L., Robin, D. A., Narayana, S., Coyle, T., Royall, D. R., Fox, P., 2009. Loss of cerebral white matter structural integrity tracks the grey matter metabolic decline in normal aging. Neuroimage 45, 17-28.
13. Tullberg, M., Fletcher, E., DeCarli, C., Mungas, D., Reed, B. R., Harvey, D. J., Weiner, M. W., Chui, H. C., Jagust, W. J., 2004. White matter lesions impair frontal lobe function regardless of their location. Neurology 63, 246-253.
14. Reed, B. R., Eberling, J. L., Mungas, D., Weiner, M., Kramer, J. H., Jagust, W. J., 2004. Effects of white matter lesions and lacunes on cortical function. Arch. Neurol. 61, 1545-1550.
15. Glodzik L, Kuceyeski A, Rusinek H, Tsui W, Mosconi L, Li Y, Osorio R S, Williams S, Randall C, Spector N, McHugh P, Murray J, Pirraglia E, Vallabhajosula S, Raj A, de Leon M J. Reduced glucose uptake and Aβ in brain regions with hyperintensities in connected white matter. Neuroimage. 2014 Oct. 15; 100:684-91

The invention claimed is:
1. An imaging-based biomarker for characterizing a structure or function of human or animal brain tissue based on an image of the human or animal brain tissue, the image showing at least one brain lesion, wherein the imaging-based biomarker is at least one chosen from the group consisting of a weighted confluency sum score and a percent shielding by brain lesions, wherein
the weighted confluency sum score is a sum of weighted confluencies over at least one brain lesion on the image, wherein the weighted confluency sum score is calculated according to formula (I):

$$WCSS = \sum_i w_i \cdot confluency_i \quad (I)$$

wherein the confluency for an $i^{th}$ brain lesion is calculated according to formula (II) or formula (III):

$$confluency_i = \sqrt[3]{\frac{1}{36 \cdot \pi} \cdot \frac{surf_i^3}{vol_i^2}} - 1 \quad (II)$$

$$confluency_i = \sqrt{\frac{1}{4 \cdot \pi} \cdot \frac{circf_i^2}{area_i}} - 1 \quad (III)$$

wherein
WCSS stands for weighted confluency sum score,
i is a summation index running over all or any subset of the brain lesions depicted on the image of the brain tissue,
$w_i$ is a weighting factor quantifying the relevance of the $i^{th}$ brain lesion for a considered application,
$surf_i$ represents an estimate of the surface area of the $i^{th}$ brain lesion,
$vol_i$ represents an estimate of the volume of the $i^{th}$ brain lesion,
$circf_i$ represents an estimate of the circumference of the $i^{th}$ brain lesion, and
$area_i$ represents an estimate of the area of the $i^{th}$ brain lesion,
wherein the confluency is a measure of a relation between a surface area of a brain lesion and a volume of the brain lesion or between a circumference of the brain lesion and an area of the brain lesion, and
wherein the percent shielding by brain lesions of a brain area is a measure for a fraction of brain lesion areas in a surrounding of a considered brain area.

2. The imaging-based biomarker according to claim 1, wherein the percent shielding by brain lesions of a brain area (A) is computed as the percentage of image voxels or image pixels in a predefined volume or area (B) surrounding the considered brain area (A) that belong to a brain lesion (BL) and calculated according to formula (IV):

$$SbBL_A = 100 * V_B(BL)/V_B \quad (IV)$$

wherein
$SbBL_A$ stands for the percent shielding by brain lesions of the considered brain area (A),
$V_B$ stands for the total number of image voxels or image pixels in a predefined volume or area (B) surrounding the considered brain area (A), and
$V_B(BL)$ stands for the number of image voxels or image pixels in B that belong to a brain lesion.

3. The imaging-based biomarker according to claim 1, wherein the image is a magnetic resonance image or a positron emission tomography image or a magnetic particle image.

4. A method for characterizing a structure or function of human or animal brain tissue, comprising the following steps:
providing an image of human or animal brain tissue, wherein the image is suited to detect brain lesions on it,
detecting at least one brain lesion on the image and delineating its outer contour,
for each delineated brain lesion, computing a confluency, the confluency being a measure of a relation between a surface area of a brain lesion and a volume of the brain lesion or between a circumference of the brain lesion and an area of the brain lesion,
computing a weighted confluency sum score as a sum of weighted confluencies over all delineated brain lesions, wherein the weighted confluency sum score is calculated according to formula (I):

$$WCSS = \sum_i w_i \cdot confluency_i, \quad (I)$$

wherein the confluency of an $i^{th}$ lesion is calculated according to formula (II) or formula (III):

$$confluency_i = \sqrt[3]{\frac{1}{36 \cdot \pi} \cdot \frac{surf_i^3}{vol_i^2}} - 1 \qquad (II)$$

$$confluency_i = \sqrt{\frac{1}{4 \cdot \pi} \cdot \frac{circf_i^2}{area_i}} - 1 \qquad (III)$$

wherein
WCSS stands for weighted confluency sum score,
i is a summation index running over all or any subset of brain lesions delineated on the image of the brain,
$w_i$ is a weighting factor quantifying the relevance of the $i^{th}$ brain lesion for a considered application,
$surf_i$ represents an estimate of the surface area of the $i^{th}$ brain lesion,
$vol_i$ represents an estimate of the volume of the $i^{th}$ brain lesion,
$circf_i$ represents an estimate of the circumference of the $i^{th}$ brain lesion, and
$area_i$ represents an estimate of the area of the $i^{th}$ brain lesion,
using the weighted confluency sum score to characterize the structure or function of the human or animal brain tissue, the image of which has been analyzed.

5. The method according to claim 4, wherein the weighting factor is different for brain lesions located within different brain regions.

6. The method according to claim 5, wherein if a brain lesion is spread over more than one brain region, the highest weighting factor of the respective brain regions is assigned to this brain lesion.

7. The method according to claim 4, wherein the weighting factor is different for brain lesions that are located within cortical grey matter, periventricular white matter, within deep white/grey matter, within subcortical white matter, or within the brain stem.

8. A method for characterizing a structure or function of human or animal brain tissue, comprising the following steps:
providing an image of human or animal brain tissue, wherein the image is suited to detect brain lesions on it,
detecting at least one brain lesion on the image and delineating its outer contour, yielding a lesion map,
computing a percent shielding by brain lesions for at least one selected brain area, wherein the percent shielding by brain lesions of a selected brain area is a measure for a fraction of a surrounding of the selected brain area belonging to brain lesions, wherein the percent shielding by brain lesions of a brain area (A) is computed as the percentage of image voxels or image pixels in a predefined volume or area (B) surrounding the considered brain area (A) that belong to a brain lesion (BL) and calculated according to formula (IV):

$$SbBL_A = 100 * V_B(BL)/V_B \qquad (IV)$$

wherein
$SbBL_A$ stands for the percent shielding by brain lesions of the considered brain area (A),
$V_B$ stands for the total number of image voxels or image pixels in a predefined volume or area (B) surrounding the considered brain area (A), and
$V_B(BL)$ stands for the number of image voxels or image pixels in B that belong to a brain lesion,
using the percent shielding by brain lesions of the at least one selected brain area to characterize the structure or function of the human or animal brain tissue, the image of which has been analyzed.

9. The method according to claim 8, wherein brain areas for computing their percent shielding by brain lesions are selected according to the following steps
providing a second image of the same human or animal brain tissue, wherein the second image is suited to provide different information about brain structure or function than the first image,
anatomically co-registering the lesion map with the second image,
stereotactically normalizing the second image together with a co-registered lesion map into an anatomical standard space to obtain a normalized second image,
comparing the normalized second image with at least one equivalent reference image from at least one reference subject to generate an effect map indicating brain areas in which a property of the second image differs from the reference image,
computing the percent shielding by brain lesions for each brain area on the effect map.

* * * * *